(12) United States Patent
Higashi et al.

(10) Patent No.: US 11,680,037 B2
(45) Date of Patent: Jun. 20, 2023

(54) BRANCHED FLUORINE-CONTAINING COMPOUND

(71) Applicant: DAIKIN INDUSTRIES, LTD., Osaka (JP)

(72) Inventors: Masahiro Higashi, Osaka (JP); Moe Hosokawa, Osaka (JP); Akiyoshi Yamauchi, Osaka (JP); Sumi Ishihara, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/387,004

(22) Filed: Jul. 28, 2021

(65) Prior Publication Data

US 2021/0355077 A1 Nov. 18, 2021

Related U.S. Application Data

(62) Division of application No. 16/332,962, filed as application No. PCT/JP2017/033115 on Sep. 13, 2017, now Pat. No. 11,104,639.

(30) Foreign Application Priority Data

Sep. 14, 2016 (JP) .................. 2016-179979

(51) Int. Cl.
| | | |
|---|---|---|
| *C07C 235/12* | (2006.01) | |
| *C07C 55/02* | (2006.01) | |
| *C07C 65/21* | (2006.01) | |
| *C07C 233/47* | (2006.01) | |

(52) U.S. Cl.
CPC ............ *C07C 235/12* (2013.01); *C07C 55/02* (2013.01); *C07C 65/21* (2013.01); *C07C 233/47* (2013.01)

(58) Field of Classification Search
CPC ....... C07C 235/12; C07C 55/02; C07C 65/21; C07C 55/32; B01F 17/0035
See application file for complete search history.

(56) References Cited

U.S. PATENT DOCUMENTS

| | | |
|---|---|---|
| 3,574,733 A | 4/1971 | Gilbert et al. |
| 3,798,265 A | 3/1974 | Bartlett et al. |
| 4,107,055 A | 8/1978 | Sukornick et al. |
| 4,292,402 A | 9/1981 | Pollet et al. |
| 5,414,017 A * | 5/1995 | Delaney ............ C07C 327/32 514/540 |
| 2006/0073607 A1 | 4/2006 | Rose et al. |
| 2011/0218353 A1 | 9/2011 | Drysdale et al. |
| 2015/0065746 A1 | 3/2015 | Nair et al. |
| 2015/0246875 A1 | 9/2015 | Friedrich et al. |
| 2016/0351839 A1 | 12/2016 | Niori |

FOREIGN PATENT DOCUMENTS

| | | |
|---|---|---|
| CA | 2 419 223 | 2/2003 |
| EP | 0 328 834 | 8/1989 |
| EP | 0 331 550 | 9/1989 |
| EP | 1 661 916 | 5/2006 |
| EP | 2 824 511 | 1/2015 |
| FR | 1.393.057 | 3/1965 |
| JP | 55-116799 | 9/1980 |
| JP | 2-59535 | 2/1990 |
| JP | 2-149589 | 6/1990 |
| JP | 3-93744 | 4/1991 |
| JP | 9-319147 | 12/1997 |
| JP | 2003-167312 | 6/2003 |
| JP | 2004-506025 | 2/2004 |

(Continued)

OTHER PUBLICATIONS

Curphey, trifluoroacetylation of amino acid and peptides by ethyl trifluoroacetate, (Journal of Organic Chemistry, vol. 44, No. 15, 1979, 2805-2807).*
Castano et al., L-aspartic acid bis (trimethylsilylester, (Tetrahedron (1992), 48 (16), 3377-3384).*
Smith et al., an enantioselective synthesis of D and L 2-amino-3-phosphonopropanoic acid, (Journal of Organic Chemistry, 1990, 55 (14), 4472-4474).*
Felker, gas-liquid chromatography of the heptafluorobutyryl-o-isobutyl esters of amino acids, (Journal of Chromatography (1978), 153 (1), 259-262, abstract).*
International Search Report dated Dec. 12, 2017 in International (PCT) Application No. PCT/JP2017/033115.

(Continued)

*Primary Examiner* — Jafar F Parsa
(74) *Attorney, Agent, or Firm* — Wenderoth, Lind & Ponack, L.L.P.

(57) ABSTRACT

A novel branched fluorine-containing compound represented by formula (1):

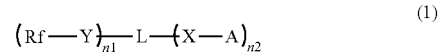

(1)

wherein L represents a predetermined carbon-containing linker moiety; Rf, in each occurrence, is the same or different and represents fluoroalkyl optionally having at least one ether bond; Y, in each occurrence, is the same or different and represents a predetermined divalent linking group or a bond; $R^Y$, in each occurrence, is the same or different and represents hydrogen or an organic group; L represents an (n1+n2)-valent carbon-containing linker moiety having at least one carbon atom; n1 represents a number greater than or equal to 1; n2 represents a number greater than or equal to 1; n1+n2 is a number from 3 to 6; X, in each occurrence, is the same or different and represents a divalent linking group or a bond; A, in each occurrence, is the same or different and represents -ArSO$_3$M or the like; M, in each occurrence, is the same or different and represents hydrogen, —NR$_4$, or a metal salt; and R represents hydrogen or a C$_{1-4}$ organic group.

15 Claims, No Drawings

(56) References Cited

FOREIGN PATENT DOCUMENTS

| | | |
|---|---|---|
| JP | 2004-131493 | 4/2004 |
| JP | 2005-91961 | 4/2005 |
| JP | 2006-56139 | 3/2006 |
| JP | 2008-23919 | 2/2008 |
| JP | 2010-80474 | 4/2010 |
| JP | 2013-503879 | 2/2013 |
| JP | 2013-195630 | 9/2013 |
| JP | 2018-22153 | 2/2018 |
| WO | 2005/073338 | 8/2005 |
| WO | 2011/028866 | 3/2011 |
| WO | 2012/061344 | 5/2012 |
| WO | 2014/012661 | 1/2014 |
| WO | 2014/095036 | 6/2014 |
| WO | 2015/133374 | 9/2015 |

OTHER PUBLICATIONS

Varvarenko et al., "Synthesis and Colloidal Properties of Polyesters Based On Glutamic Acids and Glycols of Different Nature", Chemistry & Chemical Technology, vol. 7, No. 2, 2013, pp. 161-168.

Kawase et al., "A Novel Synthesis of $SO_3H$ Type Gemini Surfactant Having Semifluoroalkyl Group as Hydrophobic Group", Journal of Oleo Science, vol. 59, No. 9, 2010, pp. 483-493.

Ohno et al., "Synthesis and properties of gemini-type hydrocarbon-fluorocarbon hybrid surfactants", Journal of Fluorine chemistry, vol. 129, 2008, pp. 577-582.

Extended European Search Report dated Sep. 9, 2020 in corresponding European Application No. 17850938.6.

Kawase et al., "Syntheses of tartaric acid-based hybrid Gemini surfactants containing fluorocarbon and hydrocarbon chains", Tenside Surfactants Detergents, 2015, vol. 52, pp. 20-28.

Ogata et al., "Molecular design of fluorescent labeled glycosides as acceptor substrates for sialyltransferases", Bioscience, Biotechnology, and Biochemistry, 2010, vol. 74, No. 11, pp. 2287-2292.

Grison et al., "Design, synthesis and activity of bisubstrate, transition-state analogues and competitive inhibitors of aspartate transcarbamylase", European Journal of Medicinal Chemistry, 2004, vol. 39, pp. 333-344.

Castaño et al., "Regioselective functionalization of chiral nickelacycles derived from N-protected aspartic and glutamic anhydrides", Tetrahedron Letters, 1990, vol. 31, No. 33, pp. 4783-4786.

Ng et al., "Exploring the use of molecular docking to identify bioaccumulative perfluorinated alkyl acids (PFAAs)", Environmental Science & Technology, vol. 49, No. 20, 2015, pp. 12306-12314.

Greaves et al., "Linear and branched perfluorooctane sulfonate (PFOS) isomer patterns differ among several tissues and blood of polar bears ", Chemosphere, vol. 93, No. 3, 2013, pp. 574-580.

Naile et al., "Isomers/enantiomers of perfluorocarboxylic acids: Method development and detection in environmental samples", Chemosphere, vol. 144, 2015, pp. 1722-1728.

O'Brien et al., "Isomer-Specific Accumulation of Perfluorooctane Sulfonate in the Liver of Chicken Embryos Exposed in Ovo to a Technical Mixture", Environmental Toxicology and Chemistry, vol. 30, No. 1, 2010, pp. 226-231.

Sharpe et al., "Perfluorooctane Sulfonate Toxicity, Isomer-Specific Accumulation, and Maternal Transfer in Zebrafish (*Danio rerio*) and Rainbow Trout (*Oncorhynchus mykiss*)", Environmental Toxicology and Chemistry, vol. 29, No. 9, 2010, pp. 1957-1966.

Riddell et al., "Branched Perfluorooctane Sulfonate Isomer Quantification and Characterization in Blood Serum Samples by HPLC/ESI-MS(/MS)", Environmental Science & Technology, vol. 43, No. 20, 2009, pp. 7902-7908.

Chu et al., "Linear and Branched Perfluorooctane Sulfonate Isomers in Technical Product and Environmental Samples by in-Port Derivatization-Gas Chromatography-Mass Spectrometry", Analytical Chemistry, vol. 81, No. 11, 2009, pp. 4256-4262.

Hidalgo et al., "Thermodynamic stability of neutral and anionic PFOAs", Theoretica Chimica Acta, vol. 134, No. 11, 2015, pp. 1-15.

Benskin et al., "Disposition of Perfluorinated Acid Isomers in Sprague-Dawley Rats; Part 1: Single Dose", Environmental Toxicology and Chemistry, vol. 28, No. 3, 2009, pp. 542-554.

Dramè et al., "Superhydrophobic and oleophobic surfaces containing wrinkles and nanoparticles of PEDOT with two short fluorinated chains", RSC Advances, vol. 4, No. 21, 2014, pp. 10935-10943.

Montero-Campillo et al., "Thermodynamic Stability of Neutral and Anionic PFOS: A Gas-Phase, n-Octanol, and Water Theoretical Study", Journal of Physical Chemistry A, vol. 114, No. 37, 2010, pp. 10148-10155.

Jeon et al., "The densely fluorinated nanospace of a porous coordination polymer composed of perfluorobutyl-functionalized ligands", Chemical Communications, vol. 50, No. 74, 2014, pp. 10861-10863.

N. Riddell et al., "LC/ESI-MS & LC/ESI-MS/MS Analysis of Individual Branched Isomers of PFOS. Differences in Response Factors and the Impact on Quantification Data for PFOS." Organohalogen Compounds, vol. 70, pp. 001321-001324, 2008.

Estelle Mayot et al., "Highly fluoroalkylated amphiphilic triazoles: Regioselective synthesis and evaluation of physicochemical properties" Journal of Fluorine Chemistry, vol. 126, Issue 5, pp. 715-720, 2005.

Kazuhiro Teramura et al., "Studies on New Textile Finishing Agents", Memoirs of the Faculty of Industrial Arts, Kyoto Technical University, Science and technology, vol. 21, pp. 41-46, 1972.

\* cited by examiner

BRANCHED FLUORINE-CONTAINING COMPOUND

TECHNICAL FIELD

The present invention relates to a branched fluorine-containing compound.

BACKGROUND ART

Patent Literature 1 discloses, as a conventional branched fluorine-containing compound, a branched fluorine-containing compound useful as a surfactant.

CITATION LIST

Patent Literature

PTL 1: WO2014/012661

SUMMARY OF INVENTION

Technical Problem

However, there is a further need to develop a branched fluorine-containing compound useful as a novel fluorine-containing surfactant (in particular, an interface promoter, a viscosity reducer, a dispersant, or an emulsifier).

Solution to Problem

The present inventors conducted extensive research, and found that the above object can be achieved by a branched fluorine-containing compound represented by formula (1):

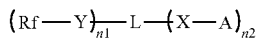
(1)

wherein
L represents (1) a trivalent carbon-containing linker moiety represented by formula (L-1-1):

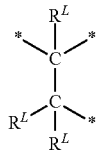
(L-1-1)

wherein $R^L$, in each occurrence, is the same or different and represents hydrogen, alkyl, —$NH_2$, —$NHR^{RL}$, —OH, or —$OR^{RL}$, and $R^{RL}$ represents an organic group,
(2) a tetravalent carbon-containing linker moiety represented by formula (L-1-2):

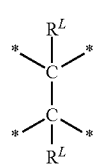
(L-1-2)

wherein $R^L$, in each occurrence, is the same or different and represents hydrogen, alkyl, —$NH_2$, —$NHR^{RL}$, —OH, or —$OR^{RL}$, and $R^{RL}$ represents an organic group,
(3) a pentavalent carbon-containing linker moiety represented by formula (L-1-3):

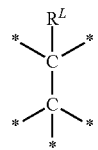
(L-1-3)

wherein $R^L$ represents hydrogen, alkyl optionally having at least one substituent, —$NH_2$, —$NHR^{RL}$, —OH, or —$OR^{RL}$, and $R^{RL}$ represents an organic group,
(4) a hexavalent carbon-containing linker moiety represented by formula (L-1-4):

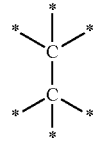
(L-1-4)

(5) a tetravalent carbon-containing linker moiety represented by formula (L-2):

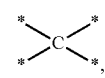
(L-2)

or
(6) an (n1+n2)-valent carbon-containing linker moiety represented by formula (L-3):

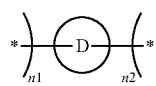
(L-3)

wherein ring D represents an aromatic ring or a non-aromatic heterocycle;
Rf, in each occurrence, is the same or different and represents fluoroalkyl optionally having at least one ether bond;
Y, in each occurrence, is the same or different and represents (1) a divalent linking group selected from the group consisting of —O—, —COO—, —OCO—, —$CONR^Y$—, and —$NR^YCO$— or (2) a bond, with the proviso that when L is a trivalent carbon-containing linker moiety represented by formula (L-1-1) or a tetravalent carbon-containing linker moiety represented by formula (L-1-2), Y is not —COO— or —OCO—;
$R^Y$, in each occurrence, is the same or different and represents hydrogen or an organic group;
L represents an (n1+n2)-valent carbon-containing linker moiety having at least one carbon atom;
n1 represents a number greater than or equal to 1;
n2 represents a number greater than or equal to 1;
n1+n2 is a number from 3 to 6;

X, in each occurrence, is the same or different and represents a divalent linking group or a bond;

A, in each occurrence, is the same or different and represents -ArSO$_3$M, —SO$_3$M, —SO$_4$M, —PO$_3$M, or —COOM;

M, in each occurrence, is the same or different and represents hydrogen, —NR$_4$, or a metal salt; and R, in each occurrence, is the same or different and represents hydrogen or a C$_{1-4}$ organic group.

The present invention has thus been accomplished.

The present invention includes the following embodiments.

Item 1. A branched fluorine-containing compound represented by formula (1):

wherein

L represents (1) a trivalent carbon-containing linker moiety represented by formula (L-1-1):

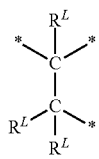

wherein R$^L$, in each occurrence, is the same or different and represents hydrogen, alkyl optionally having at least one substituent, —NH$_2$, —NHR$^{RL}$, —OH, or —OR$^{RL}$, and R$^{RL}$ represents an organic group, (2) a tetravalent carbon-containing linker moiety represented by formula (L-1-2):

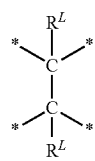

wherein R$^L$, in each occurrence, is the same or different and represents hydrogen, alkyl optionally having at least one substituent, —NH$_2$, —NHR$^{RL}$, —OH, or —OR$^{RL}$, and R$^{RL}$ represents an organic group, (3) a pentavalent carbon-containing linker moiety represented by formula (L-1-2):

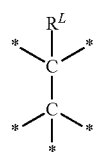

wherein R$^L$ represents hydrogen, alkyl optionally having at least one substituent, —NH$_2$, —NHR$^{RL}$, —OH, or —OR$^{RL}$, and R$^{RL}$ represents an organic group, (4) a hexavalent carbon-containing linker moiety represented by formula (L-1-2):

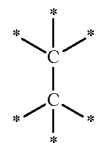

(5) a tetravalent carbon-containing linker moiety represented by formula (L-2):

or (6) an (n1+n2)-valent carbon-containing linker moiety represented by formula (L-3):

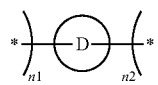

wherein ring D represents an aromatic ring or a non-aromatic heterocycle;

Rf, in each occurrence, is the same or different and represents fluoroalkyl optionally having at least one ether bond;

Y, in each occurrence, is the same or different and represents (1) a divalent linking group selected from the group consisting of —O—, —COO—, —OCO—, —CONR$^Y$—, and —NR$^Y$CO— or (2) a bond, with the proviso that when L is a trivalent carbon-containing linker moiety represented by formula (L-1-1) or a tetravalent carbon-containing linker moiety represented by formula (L-1-2), Y is not —COO— or —OCO—;

R$^Y$, in each occurrence, is the same or different and represents hydrogen or an organic group;

L represents an (n1+n2)-valent carbon-containing linker moiety having at least one carbon atom;

n1 represents a number greater than or equal to 1;

n2 represents a number greater than or equal to 1;

n1+n2 is a number from 3 to 6;

X, in each occurrence, is the same or different and represents a divalent linking group or a bond;

A, in each occurrence, is the same or different and represents -ArSO$_3$M, —SO$_3$M, —SO$_4$M, —PO$_3$M, or —COOM;

M, in each occurrence, is the same or different and represents hydrogen, —NR$_4$, or a metal salt; and R represents hydrogen or a C$_{1-4}$ organic group.

Item 2. The branched fluorine-containing compound according to Item 1, wherein L is a trivalent carbon-containing linker moiety represented by formula (L-1-1) or a tetravalent carbon-containing linker moiety represented by formula (L-1-2); and Y, in each occurrence, is the same or different and represents (1) a divalent linking group selected from the group consisting of —O—, —CONR$^Y$—, and —NR$^Y$CO— or (2) a bond.

Item 3. The branched fluorine-containing compound according to Item 2, wherein X is an alkylene chain or a bond.
Item 4. The branched fluorine-containing compound according to Item 3, wherein X is a bond.
Item 5. The branched fluorine-containing compound according to Item 1, wherein L is a tetravalent carbon-containing linker moiety represented by formula (L-2); and at least one Y is —O—, —COO—, —OCO—, —CONR$^Y$—, or —NR$^Y$CO—.
Item 6. The branched fluorine-containing compound according to any one of Items 1 to 4, wherein n1 is 1 or 2; and n2 is 2.

The present invention further includes the following embodiments.
Item 7. A surfactant comprising the branched fluorine-containing compound according to any one of Items 1 to 6.
Item 8. An aqueous dispersant comprising the branched fluorine-containing compound according to any one of Items 1 to 6.

Advantageous Effects of Invention

The present invention provides a novel branched fluorine-containing compound.
In an embodiment of the present invention, the branched fluorine-containing compound is useful as an emulsifier.

DESCRIPTION OF EMBODIMENTS

Terms

The symbols and the abbreviations in this specification are to be interpreted as having the general meanings in the related technical field to which the present invention pertains, according to the context of this specification, unless otherwise specified.
In this specification, the term "comprise" or "contain" is intended to encompass the meanings of "consist essentially of" and "consist of."
The steps, treatments, or operations in this specification can be performed at room temperature, unless otherwise specified.
In this specification, room temperature refers to a temperature in the range of 10 to 40° C.
In this specification, the term "Cn-m" (herein, n and m are numbers) indicates that the carbon number is n or more and m or less, as usually understood by a person skilled in the art.
In this specification, unless otherwise specified, examples of "halogen atom" include fluorine, chlorine, bromine, and iodine.
In this specification, the term "organic group" refers to a group containing at least one carbon atom, or a group formed by removing one hydrogen atom from an organic compound.
Examples of "organic group" include the following:
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
non-aromatic heterocyclic group optionally having at least one substituent,
heteroaryl optionally having at least one substituent,
cyano,
aldehyde,
R$^a$O—,
R$^a$CO—,
R$^a$SO$_2$—,
R$^a$OCO—, and
R$^a$OSO$_2$—
wherein R$^a$ is independently
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
non-aromatic heterocyclic group optionally having at least one substituent, or
heteroaryl optionally having at least one substituent.

In this specification, examples of the substituent in each of alkyl optionally having at least one substituent, alkenyl optionally having at least one substituent, alkynyl optionally having at least one substituent, cycloalkyl optionally having at least one substituent, cycloalkenyl optionally having at least one substituent, cycloalkadienyl optionally having at least one substituent, aryl optionally having at least one substituent, aralkyl optionally having at least one substituent, non-aromatic heterocyclic group optionally having at least one substituent, and heteroaryl optionally having at least one substituent include nitro, hydroxy, halogen, cyano, aliphatic group, aryl, heterocyclyl, acyl, acyloxy, acylamino, aliphatic oxy, aryloxy, heterocyclyloxy, aliphatic oxycarbonyl, aryloxycarbonyl, heterocyclyloxycarbonyl, carbamoyl, aliphatic sulfonyl, arylsulfonyl, heterocyclylsulfonyl, aliphatic sulfonyloxy, arylsulfonyloxy, heterocyclylsulfonyloxy, sulfamoyl, aliphatic sulfonamide, arylsulfonamide, heterocyclylsulfonamide, amino, aliphatic amino, arylamino, heterocyclylamino, aliphatic oxycarbonylamino, aryloxycarbonylamino, heterocyclyloxycarbonylamino, aliphatic sulfinyl, arylsulfinyl, aliphatic thio, arylthio, sulfo, carboxy, aliphatic oxyamino, aryloxyamino, carbamoylamino, sulfamoylamino, halogen, sulfamoylcarbamoyl, carbamoylsulfamoyl, dialiphatic oxyphosphinyl, and diaryloxyphosphinyl (the group consisting of these substituents may be referred to as "substituent group A"); and preferably include
(a) halogen,
(b) hydroxy,
(c) nitro, and
(d) cyano.

The term "aryl" in the substituent group A can mean an aryl group or an aryl moiety.
The term "aliphatic" in the substituent group A can mean an aliphatic group or an aliphatic moiety.
In substituents or part thereof of the substituent group A, the term "aliphatic (group or moiety)" may have at least one substituent, and may be saturated or unsaturated.
The substituent may be any group with which the "aliphatic (group or moiety)" can be substituted, among the substituent group A.
Examples of the substituent include hydroxy, aliphatic oxy, carbamoyl, aliphatic oxycarbonyl, aliphatic thio, amino, aliphatic amino, acylamino, and carbamoylamino.
The term "aliphatic (group or moiety)" is preferably C$_{1-8}$ alkyl, and more preferably C$_{1-4}$ alkyl. Examples of "aliphatic (group or moiety)" include methyl, ethyl, vinyl, cyclohexyl, and carbamoylmethyl.

In substituents or part thereof of the substituent group A, the "aryl (group or moiety)" may be fused with at least one ring (e.g., a 3- to 8-membered non-aromatic heterocycle, a 5- or 6-membered aromatic heterocycle, a $C_{3-8}$ non-aromatic carbocycle), and may have a substituent(s).

The substituent may be any group with which the "aryl (group or moiety)" can be substituted, among the substituent group A.

Examples of the substituent include nitro, halogen, aliphatic oxy, carbamoyl, aliphatic oxycarbonyl, aliphatic thio, amino, aliphatic amino, acylamino, and carbamoylamino.

The term "aryl (group or moiety)" is preferably $C_{6-12}$ aryl, and more preferably $C_{6-10}$ aryl.

Examples of "aryl (group or moiety)" include phenyl, 4-nitrophenyl, 4-acetylaminophenyl, and 4-methanesulfonylphenyl.

In substituents or part thereof of the substituent group A, the term "heterocyclyl (group or moiety)" may have a substituent(s), may be saturated or unsaturated, and may be fused with a ring(s). Specifically, the term "heterocyclyl (group or moiety)" may be the aforementioned non-aromatic heterocyclic group or heteroaryl.

The substituent may be any group with which the "heterocyclyl (group or moiety)" can be substituted, among the substituent group A.

Examples of the substituent include halogen, hydroxy, aliphatic oxy, carbamoyl, aliphatic oxycarbonyl, aliphatic thio, amino, aliphatic amino, acylamino, and carbamoylamino.

In substituents or part thereof of the substituent group A, the term "heterocyclyl (group or moiety)" is preferably $C_{2-12}$ 5- to 14-membered heterocyclyl that is bonded via a carbon atom thereof, and more preferably $C_{2-10}$ 5- to 14-membered heterocyclyl that is bonded via a carbon atom thereof.

Examples of "heterocyclyl (group or moiety)" include 2-tetrahydrofuryl and 2-pyrimidyl.

In substituents or part thereof of the substituent group A, the term "acyl (group or moiety)" may be aliphatic carbonyl, arylcarbonyl, or heterocyclylcarbonyl, and may have a substituent(s).

The substituent may be any group with which the "acyl (group or moiety)" can be substituted, among the substituent group A.

Examples of the substituent include hydroxy, halogen, aryl, aliphatic oxy, carbamoyl, aliphatic oxycarbonyl, aliphatic thio, amino, aliphatic amino, acylamino, and carbamoylamino.

The term "acyl (group or moiety)" is preferably $C_{2-8}$ acyl, and more preferably $C_{2-4}$ acyl.

Examples of "acyl (group or moiety)" include acetyl, propanoyl, benzoyl, and 3-pyridinecarbonyl.

In substituents or part thereof of the substituent group A, the term "carbamoyl (group or moiety)" may have a substituent(s).

The substituent may be any group with which the "carbamoyl (group or moiety)" can be substituted, among the substituent group A.

Examples of the substituent include an aliphatic group, aryl, and heterocyclyl.

The term "carbamoyl" is preferably unsubstituted carbamoyl or alkylcarbamoyl having a total of 2 to 9 (preferably 2 to 5) carbon atoms.

Examples of "carbamoyl" include N-methylcarbamoyl, N,N-dimethylcarbamoyl, and N-phenylcarbamoyl.

In this specification, examples of the substituent in each of cycloalkyl optionally having at least one substituent, cycloalkenyl optionally having at least one substituent, cycloalkadienyl optionally having at least one substituent, aryl optionally having at least one substituent, aralkyl optionally having at least one substituent, non-aromatic heterocyclic group optionally having at least one substituent, and heteroaryl optionally having at least one substituent further include (e) alkyl optionally having at least one substituent,
(f) alkenyl optionally having at least one substituent, and
(g) alkynyl optionally having at least one substituent.

In this specification, unless otherwise specified, the term "alkyl" may be linear or branched.

In this specification, unless otherwise specified, preferable examples of "alkyl" include $C_{1-20}$ alkyl, $C_{1-8}$ alkyl, $C_{1-7}$ alkyl, $C_{1-6}$ alkyl, and $C_{1-5}$ alkyl.

In this specification, unless otherwise specified, specific examples of "alkyl" include methyl, ethyl, propyl, isopropyl, butyl, isobutyl, sec-butyl, tert-butyl, pentyl, isopentyl, neopentyl, hexyl, heptyl, octyl, nonyl, and decyl.

In this specification, specific examples of "$C_{1-8}$ alkyl" include alkyl having 1 to 8 carbon atoms among the aforementioned specific examples of alkyl, as naturally understood by a person skilled in the art. As a precaution, specific examples of "$C_{1-8}$ alkyl" include linear or branched $C_{1-8}$ alkyl.

In this specification, the term "fluoroalkyl optionally having at least one ether bond" may be fluoroalkyl into which at least one etheric oxygen atom may be inserted.

Examples thereof include
(1) alkyl substituted with at least one fluorine atom; and
(2) alkyl having at least one ether bond and substituted with at least one fluorine atom.

In this specification, the term "fluoroalkyl" encompasses perfluoroalkyl.

In this specification, specific examples of "fluoroalkyl" include $CF_3$—, $C_2F_5$—, $C_3F_7$—, $C_2F_5CH_2$—, $H(CF_2CF_2)_2CH_2$—, and $H(CF_2CF_2)_3CH_2$—.

In this specification, specific examples of fluoroalkyl having at least one ether bond include $CF_3OC_2F_4$—, $CF_3OC_3F_6$—, $CF_3OC_4F_8$—, $CF_3OC_5F_{10}$—, $CF_3OC_2F_4OC_2F_4$—, $C_2F_5OC_2F_4$—, $C_2F_5OC_3F_6$—, $C_2F_5OC_4F_8$—, $C_2F_5OC_2F_4OC_2F_4$—, $C_3F_7O(CF_2)_2$—, $C_3F_7OCF(CF_3)$—, $C_3F_7OC_3F_6$—, and $C_4F_9OC_2F_4$—.

In this specification, unless otherwise specified, examples of "alkenyl" include linear or branched $C_{2-10}$ alkenyl, such as vinyl, 1-propen-1-yl, 2-propen-1-yl, isopropenyl, 2-buten-1-yl, 4-penten-1-yl, and 5-hexen-1-yl.

In this specification, unless otherwise specified, examples of "alkynyl" include linear or branched $C_{2-10}$ alkynyl, such as ethynyl, 1-propyn-1-yl, 2-propyn-1-yl, 4-pentyn-1-yl, and 5-hexyne-1-yl.

In this specification, unless otherwise specified, examples of "cycloalkyl" include $C_{3-10}$ cycloalkyl, such as cyclopropyl, cyclobutyl, cyclopentyl, cyclohexyl, and cycloheptyl.

In this specification, unless otherwise specified, examples of "cycloalkenyl" include $C_{3-10}$ cycloalkenyl, such as cyclopropenyl, cyclobutenyl, cyclopentenyl, cyclohexenyl, and cycloheptenyl.

In this specification, unless otherwise specified, examples of "cycloalkadienyl" include $C_{4-10}$ cycloalkadienyl, such as cyclobutadienyl, cyclopentadienyl, cyclohexadienyl, cycloheptadienyl, cyclooctadienyl, cyclononadienyl, and cyclodecadienyl.

In this specification, unless otherwise specified, the term "aryl" may be monocyclic, bicyclic, tricyclic, or tetracyclic.

In this specification, unless otherwise specified, the term "aryl" may be $C_{6-18}$ aryl.

In this specification, unless otherwise specified, examples of "aryl" include phenyl, 1-naphthyl, 2-naphthyl, 2-biphenyl, 3-biphenyl, 4-biphenyl, and 2-anthryl.

In this specification, unless otherwise specified, examples of "aralkyl" include benzyl, phenethyl, diphenylmethyl, 1-naphthyl methyl, 2-naphthyl methyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In this specification, unless otherwise specified, the term "non-aromatic heterocyclic group" may be monocyclic, bicyclic, tricyclic, or tetracyclic.

In this specification, unless otherwise specified, the term "non-aromatic heterocyclic group" may be, for example, a non-aromatic heterocyclic group containing, in addition to carbon, 1 to 4 heteroatoms selected from oxygen, sulfur, and nitrogen as a ring-constituting atom.

In this specification, unless otherwise specified, the term "non-aromatic heterocyclic group" may be saturated or unsaturated.

In this specification, unless otherwise specified, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

In this specification, unless otherwise specified, the term "heteroaryl" may be, for example, a monocyclic, bicyclic, tricyclic, or tetracyclic, 5- to 18-membered heteroaryl.

In this specification, unless otherwise specified, the term "heteroaryl" is, for example, heteroaryl containing, in addition to carbon, 1 to 4 heteroatoms selected from oxygen, sulfur, and nitrogen as a ring-constituting atom. The term "heteroaryl" may have, for example, 3 to 17 carbon atoms.

In this specification, unless otherwise specified, the term "heteroaryl" encompasses monocyclic heteroaryl and aromatic fused heterocyclic group.

In this specification, unless otherwise specified, examples of "monocyclic heteroaryl" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

In this specification, unless otherwise specified, examples of "aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like.

In this specification, unless otherwise specified, examples of aromatic rings include aromatic carbocycles and aromatic heterocycles.

In this specification, unless otherwise specified, examples of aromatic carbocycles include a benzene ring, a naphthalene ring, and an anthracene ring.

In this specification, unless otherwise specified, examples of aromatic heterocycles include
(1) 5- or 6-membered aromatic heterocycles; specific examples thereof include a furan ring, a thiophene ring, a pyrrole ring, an oxazole ring, an isoxazole ring, a triazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring, and the like;

(2) rings formed by fusing two of the aforementioned 5- or 6-membered aromatic heterocycles; and (3) rings formed by fusing one of the aforementioned 5- or 6-membered aromatic heterocycles and a benzene ring.

In this specification, unless otherwise specified, examples of non-aromatic heterocycles include 3- to 8-membered non-aromatic heterocycles containing, in addition to carbon, 1 to 4 heteroatoms selected from oxygen, sulfur, and nitrogen as a ring-constituting atom, and the like. Specific examples thereof include oxirane, azetidine, oxetane, thietane, pyrrolidine, dihydrofuran, tetrahydrofuran, tetrahydrothiophene, imidazolidine, oxazolidine, isoxazoline, piperidine, dihydropyran, tetrahydropyran, tetrahydrothiopyran, morpholine, thiomorpholine, piperazine, dihydrooxazine, tetrahydrooxazine, dihydropyrimidine, tetrahydropyrimidine, azepane, oxetane, thiepane, oxazepane, thiazepane, azocane, oxocane, thiocane, oxazocane, thiazocane, and the like.

In this specification, examples of "alkali metal" include lithium, sodium, potassium, rubidium, and cesium.

In this specification, the term "alkylene chain" may be a divalent group formed by removing one hydrogen atom from the alkyl described above.

Compound

The compound of the present invention is a branched fluorine-containing compound represented by formula (1) (which may be referred to as "compound (1)" in this specification).

The symbols in formula (1) are explained below.

L represents (1) a trivalent carbon-containing linker moiety represented by formula (L-1-1):

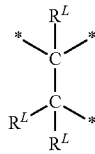

(L-1-1)

wherein $R^L$, in each occurrence, is the same or different and represents hydrogen, alkyl optionally having at least one substituent, —NH$_2$, —NHR$^{RL}$, —OH, or —OR$^{RL}$, and R$^{RL}$ represents an organic group, (2) a tetravalent carbon-containing linker moiety represented by formula (L-1-2):

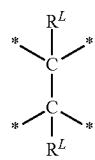

(L-1-2)

wherein $R^L$, in each occurrence, is the same or different and represents hydrogen, alkyl optionally having at least one substituent, —NH$_2$, —NHR$^{RL}$, —OH, or —OR$^{RL}$, and R$^{RL}$ represents a substituent, (3) a pentavalent carbon-containing linker moiety represented by formula (L-1-3):

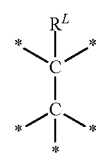

(L-1-3)

wherein $R^L$ represents hydrogen, alkyl optionally having at least one substituent, —NH$_2$, —NHR$^{RL}$, —OH, or —OR$^{RL}$, and R$^{RL}$ represents an organic group, (4) a hexavalent carbon-containing linker moiety represented by formula (L-1-4):

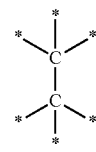

(L-1-4)

(5) a tetravalent carbon-containing linker moiety represented by formula (L-2):

(L-2)

or (6) an (n1+n2)-valent carbon-containing aromatic linker moiety represented by formula (L-3):

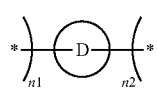

(L-3)

wherein ring D represents an aromatic ring.

In each of these partial structural formulas, the alkyl of "alkyl optionally having at least one substituent" represented by $R^L$ is the same or different and is preferably C$_{1-10}$ alkyl.

Among the carbon-containing linker moieties represented by formulas (L-1-1), (L-1-2), (L-1-3), and (L-1-4), a trivalent carbon-containing linker moiety represented by formula (L-1-1) or a tetravalent carbon-containing linker moiety represented by formula (L-1-2) is preferable.

n1 is a number greater than or equal to 1 (preferably a number from 1 to 5).

n1 may be, for example, 1, 2, 3, or 4 (preferably 1 or 2, and more preferably 2).

n2 is a number greater than or equal to 1 (preferably a number from 1 to 5).

n2 may be, for example, 1, 2, 3, or 4 (preferably 1 or 2, and more preferably 2).

n1+n2 may be, for example, 3, 4, 5, or 6 (preferably 3 or 4).

In another preferred embodiment of the present invention,
L is a linker moiety represented by formula (L-1-1), (L-1-2), (L-2), or (L-3);
n1 is 1 or 2; and
n2 is 2.

In another preferred embodiment of the present invention,
L is a linker moiety represented by formula (L-1-2), (L-2), or (L-3) (preferably formula (L-1-2));
n1+n2 is 4; and
(a) n1 is 3, and n2 is 1, or
(b) n1 is 1, and n2 is 3.

In another preferred embodiment of the present invention,
L is a linker moiety represented by formula (L-1-3) or (L-3) (preferably formula (L-1-3));
n1+n2 is 5; and
(a) n1 is 4, and n2 is 1,
(b) n1 is 3, and n2 is 2,
(c) n1 is 2, and n2 is 3, or
(d) n1 is 1, and n2 is 4.

In another preferred embodiment of the present invention,
L is a linker moiety represented by formula (L-1-4) or (L-3) (preferably formula (L-1-4));
n1+n2 is 6; and
(a) n1 is 5, and n2 is 1,
(b) n1 is 4, and n2 is 2,
(c) n1 is 3, and n2 is 3,
(d) n1 is 2, and n2 is 4, or
(e) n1 is 1, and n2 is 5.

In another preferred embodiment of the present invention,
L is a linker moiety represented by formula (L-1-2), (L-2), or (L-3);
n1 is 3; and
n2 is 1.

The direction of the partial structural formula of formula (L-1-1), (L-1-2), (L-2), or (L-3), and the direction of the structural formula of formula (1) may be the same or different.

Thus, as easily understood by a person skilled in the art, the asterisks (*) in formula (L-1-1), (L-1-2), (L-2), or (L-3) each independently represent a bonding site to Rf-Y— or —X-A.

In a preferred embodiment of compound (1) having a carbon-containing linker moiety represented by formula (L-1-1), compound (1) has two Rf-Y— groups, and has a structure represented by the following formula (1-L-1-1A):

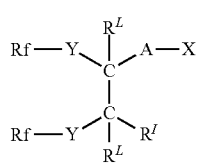

(1-L-1-1A)

wherein the symbols in the formula are as defined above.

In a preferred embodiment of compound (1) having a carbon-containing linker moiety represented by formula (L-1-1), compound (1) has two —X-A groups, and has a structure represented by the following formula (1-L-1-1B):

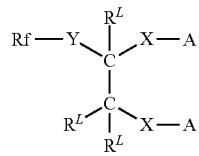

(1-L-1-1B)

wherein the symbols in the formula are as defined above.

In a preferred embodiment of compound (1) having a carbon-containing linker moiety represented by formula (L-1-2), compound (1) has two Rf-Y— groups and two —X-A groups, and has a structure represented by the following formula (1-L-1-2):

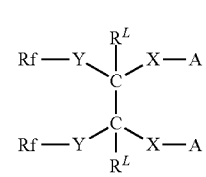

(1-L-1-2)

wherein the symbols in the formula are as defined above.

In a preferred embodiment of compound (1) having a carbon-containing linker moiety represented by formula (L-2), compound (1) has two Rf-Y— groups and two —X-A groups, and a carbon-containing linker moiety derived from a benzene ring, and has a structure represented by the following formula (1-2):

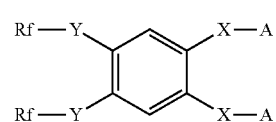

(1-L-2)

wherein the symbols in the formula are as defined above.

Rf, in each occurrence, is the same or different and represents fluoroalkyl optionally having at least one ether bond.

Rf, in each occurrence, is the same or different and is preferably $C_{1-20}$ fluoroalkyl optionally having at least one ether bond, more preferably $C_{1-8}$ fluoroalkyl optionally having at least one ether bond, even more preferably $C_{1-7}$ fluoroalkyl optionally having at least one ether bond, still even more preferably $C_{1-6}$ fluoroalkyl optionally having at least one ether bond, and particularly preferably $C_{1-5}$ fluoroalkyl optionally having at least one ether bond.

Rf is preferably fluoroalkyl containing a $C_{1-5}$ perfluoroalkyl moiety (which may have at least one ether bond).

Y, in each occurrence, is the same or different and represents (1) a divalent linking group selected from the group consisting of —O—, —OCO—, —OCO—, —CONR$^Y$—, and —NR$^Y$CO— or (2) a bond, with the proviso that when L is a linker moiety represented by formula (L-1-1) or (L-1-2), Y is not —COO— or —OCO—.

In a preferred embodiment of the present invention,
L is a trivalent carbon-containing linker moiety represented by formula (L-1-1) or a tetravalent carbon-containing linker moiety represented by formula (L-1-2); and
preferably, Y, in each occurrence, is the same or different (preferably, in each occurrence, is the same) and represents (1) a divalent linking group selected from the group consisting of —O—, —CONR$^Y$—, and —NR$^Y$CO— or (2) a bond.

The compound of this embodiment is particularly excellent in stability (in particular, under acidic or basic conditions).

R$^Y$, in each occurrence, is the same or different (preferably, in each occurrence, is the same) and represents hydrogen or an organic group.

Preferably, R$^Y$, in each occurrence, is the same or different (preferably, in each occurrence, is the same) and represents methyl, trifluoromethyl or hydrogen.

R$^Y$ is more preferably hydrogen.

More preferably, Y, in each occurrence, is the same or different (preferably, in each occurrence, is the same) and represents —CONH—, —NHCO—, or —O—.

X, in each occurrence, is the same or different and represents a divalent linking group or a bond.

Preferably, X, in each occurrence, is the same or different (preferably, in each occurrence, is the same) and represents an alkylene chain or a bond.

X is more preferably a bond.

In a preferred embodiment of the present invention, L is a tetravalent carbon-containing linker moiety represented by formula (L-2); and at least one Y is —O—, —COO—, —OCO—, —CONR$^Y$—, or —NR$^Y$CO—.

In a preferred embodiment of the present invention,
n1 is 1 or 2; and
n2 is 2.

A, in each occurrence, is the same or different (preferably, in each occurrence, is the same) and represents -ArSO$_3$M, —SO$_3$M, —SO$_4$M, —PO$_3$M, or —COOM.

A is preferably —COOM or —SO$_4$M, and more preferably —COOM.

M, in each occurrence, is the same or different (preferably, in each occurrence, is the same) and represents hydrogen, —NR$_4$, or a metal salt.

R, in each occurrence, is the same or different and represents hydrogen or a C$_{1-4}$ organic group.

M is preferably —NH$_4$.

The compound of a particularly preferred embodiment of the present invention is a branched fluorine-containing compound represented by the following:

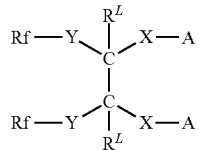

(1-L-1-1B)

wherein
Rf, in each occurrence, is the same or different and represents fluoroalkyl optionally having at least one ether bond;
Y, in each occurrence, is the same or different and represents (1) a divalent linking group selected from the group consisting of —O—, —CONH—, and —NHCO— or (2) a bond;
X represents a bond; and
A represents —COONH$_4$.

The compound of another particularly preferred embodiment of the present invention is a branched fluorine-containing compound represented by the following:

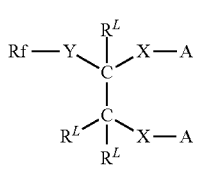

(1-L-1-2)

wherein
Rf, in each occurrence, is the same or different and represents fluoroalkyl optionally having at least one ether bond;
Y, in each occurrence, is the same or different and represents (1) a divalent linking group selected from the group consisting of —O—, —CONH—, and —NHCO— or (2) a bond;
X represents a bond; and
A represents —COONH$_4$.

The compound of still another particularly preferred embodiment of the present invention is a branched fluorine-containing compound represented by the following:

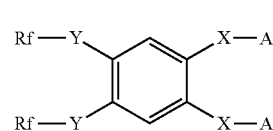

(1-L-2)

wherein
Rf, in each occurrence, is the same or different and represents fluoroalkyl optionally having at least one ether bond;
Y, in each occurrence, is the same or different and represents (1) a divalent linking group selected from the group consisting of —O—, —CONH—, and —NHCO— or (2) a bond;
X represents a bond; and
A represents —COONH$_4$.

Synthesis Method for Compound

The compound of the present invention can be synthesized by a known method, a method similar to a known method, or a combination thereof.

Specifically, for example, compound (1) of the present invention in which A is —COONH$_4$ can be synthesized by, for instance, adding an ammonia methanol solution to a compound of formula (1) in which A is —COOH. The compound of formula (1) in which A is —COOH can be produced according to a known method, or is commercially available.

Specifically, for example, compound (1) having a carbon-containing linker moiety represented by formula (L-1-1), (L-1-2), (L-2), or (L-3) can be synthesized by causing a base to act on a carboxylic acid having the carbon-containing linker moiety or an ester thereof (e.g., dihydroxysuccinic acid (tartaric acid), methyl dihydroxysuccinate, monoaminosuccinic acid (aspartic acid), diaminosuccinic acid, or diethyl malonate) as necessary, and then adding a fluorine-containing compound (e.g., CF$_3$COOCOCF$_3$, CF$_3$COOCH$_3$, C$_3$F$_7$OCF(CF$_3$) COOCH$_3$, CF$_2$=CFOCF$_2$CF$_2$CF$_3$, and CF$_3$CF$_2$CF$_2$CF$_2$CH$_2$CH$_2$I) as an electrophile. Such a carboxylic acid or an ester thereof can be produced according to a known method, or is commercially available.

The compound of the present invention can suitably decrease the surface tension of water.

The compound of the present invention can be suitably used as a surfactant.

The compound of the present invention can be suitably used as an interface promoter (in particular, an interface promoter in, for example, coating materials, lacquers, or adhesives).

The compound of the present invention can also be suitably used as, for example, a viscosity reducer.

The compound of the present invention can also be suitably used as, for example, a dispersant, in particular, an aqueous dispersant.

The compound of the present invention can also be suitably used as, for example, an emulsifier.

Surfactant

The present invention also provides a surfactant containing the compound of the present invention described above. The compound of the present invention can be an active ingredient of the surfactant.

An aspect of the present invention can be a method for activating an interface, comprising using the compound of the present invention.

The surfactant of the present invention may contain a substance(s) other than the compound of the present invention. Examples of such substances include hydrocarbon-based surfactants.

Examples of hydrocarbon-based surfactants include compounds of formula: R-Y-M (wherein R is $C_{6-17}$ alkyl, Y is -ArSO$_3$—, —SO$_3$—, —SO$_4$—, —PO$_3$—, or —COO—, Ar is aryl, and M is $H^+$, $Na^+$, $K^+$, or $NH_4^+$).

Specific examples of hydrocarbon-based surfactants include sodium dodecyl sulfate.

Such hydrocarbon-based surfactants are, for example, commercially available.

Hydrocarbon surfactants encompass anionic hydrocarbon surfactants, nonionic hydrocarbon surfactants, and cationic surfactants.

The following surfactants, including commercially available surfactants, are examples of hydrocarbon surfactants.

[1] Examples of anionic hydrocarbon surfactants include the following:
(1) Versatic 10 (trade name, Resolution Performance Products), which is a highly branched C10 tertiary carboxylic acid;
(2) Avanel S series (trade name, BASF), which are sodium linear alkyl polyether sulfonates;
(3) Lankropol K8300 (trade name, Akzo Nobel Surface Chemistry), which is a sulfosuccinate surfactant;
(4) (i) Emulsogen SB10 (trade name, Clariant) and (ii) Polirol (trade name) TR/LNA (trade name, Cesalpinia Chemicals), which are diisodecyl sulfosuccinate, Na salt;
(5) SilSense PE-100 Silicone (trade name, Noveon Consumer Specialties) and SilSense CA-A Silicone (trade name, Noveon Consumer Specialties), which are siloxane-based and anionic hydrocarbon surfactants; and
(6) sodium dodecyl sulfate (SDS).

[2] Examples of nonionic hydrocarbon surfactants, which are hydrocarbon surfactants, include the following:
(1) Triton X (trade name, Dow Chemical) series, which are octylphenol ethoxylates;
(2) Tergitol 15-S (trade name, Dow Chemical) series, which are branched alcohol ethoxylates;
(3) Dow Tergitol TMN (trade name, Dow Chemical) series, which are branched secondary alcohol ethoxylates;
(4) Tergitol L (trade name, Dow Chemical) series, which are ethylene oxide/propylene oxide copolymers;
(5) Pluronic R (trade name, BASF) series, which are difunctional block copolymers; and
(6) TDA (trade name, BASF) series, which are tridecyl alcohol alkoxylates.

[3] Examples of cationic surfactants, which are hydrocarbon surfactants, include cetyltrimethylammonium bromide (CTMAB).

The present invention also provides an aqueous dispersant containing the compound of the present invention described above. The compound of the present invention can be an active ingredient of the aqueous dispersant.

An aspect of the present invention can be a method for dispersing an object to be dispersed in an aqueous system, comprising using the compound of the present invention.

EXAMPLES

Examples are given below to illustrate the present invention in more detail; however, the present invention is not limited to these Examples.

The symbols and abbreviations in the Examples are defined as follows.
AIBN: azobisisobutyronitrile Synthesis Examples Synthesis Example 1

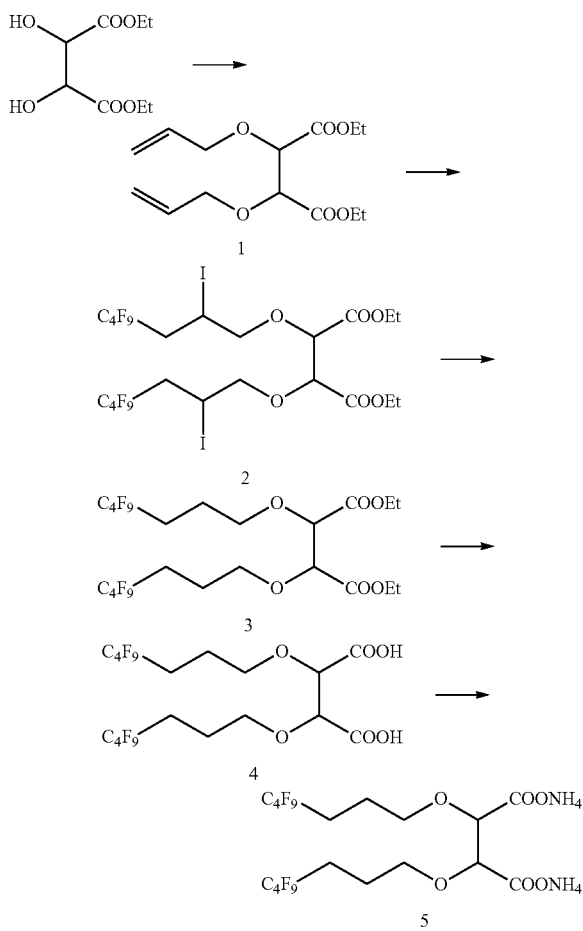

Allyl bromide (1.7 eq.) and silver oxide (2.0 eq.) were added to a diethyl ether solution (100 mL) of diethyl tartrate (4.9 g), and the mixture was stirred at 50° C. for 2 hours. Further, the mixture was stirred at room temperature for 7 days. The reaction mixture was filtered, and the filtrate was concentrated to give compound 1 (6.3 g, 92%).

A solution obtained by adding $C_4F_9I$ (2.4 eq.) and AIBN (0.2 eq.) to compound 1 (2.3 g) was heated at 80° C. for 18 hours. After the reaction, water was added, followed by extraction with chloroform. The solvent was distilled off from the extract to give compound 2 (6.0 g, 76%).

Water and NMP were added to sodium hydrogen carbonate (2.0 eq.) and sodium hydrosulfite (2.0 eq.), and the mixture was stirred. Further, compound 2 (6.0 g) was added dropwise thereto, and the mixture was stirred for 12 hours. Aqueous hydrochloric acid was added to the reaction mixture, followed by extraction with dichloromethane. The solvent was distilled off from the extract to give compound 3 (2.2 g, 49%).

An aqueous sodium hydroxide solution (2.0 eq.) was added to a methanol solution (10 mL) of compound 3 (2.2 g), and the mixture was stirred at room temperature for 12 hours. Aqueous hydrochloric acid was added to the reaction product solution, followed by extraction with ethyl acetate. The solvent was distilled off from the extract to give compound 4 (1.4 g, 71%).

An ammonia methanol solution (2.0 eq.) was added to a methanol solution (10 mL) of compound 4 (1.4 g), and the mixture was stirred at room temperature for 1 hour. After the reaction, the solvent was distilled off to give compound 5 (1.5 g, quant.).

Synthesis Example 2

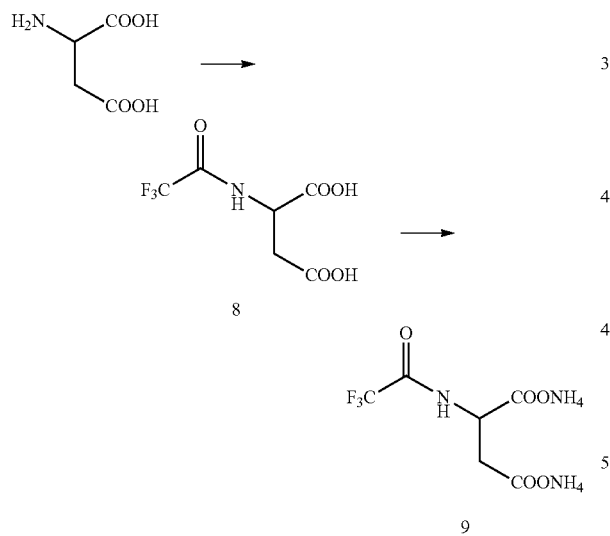

CF3COOCH3 (1.3 eq.) and triethylamine (2.0 eq.) were added to a methanol solution (10 mL) of monoaminosuccinic acid (13 g), and the mixture was stirred at room temperature for 17 hours. 1N aqueous hydrochloric acid was added to the reaction mixture, and the mixture was extracted with ethyl acetate. The solvent was distilled off from the extract, and the crude product was recrystallized to give compound 8 (10 g, 44%).

An ammonia methanol solution (4.0 eq.) was added to a methanol solution (10 mL) of compound 8 (10 g), and the mixture was stirred at room temperature for 1 hour. Thereafter, the solvent was distilled off to give compound 9 (12 g, quant.).

Synthesis Example 3

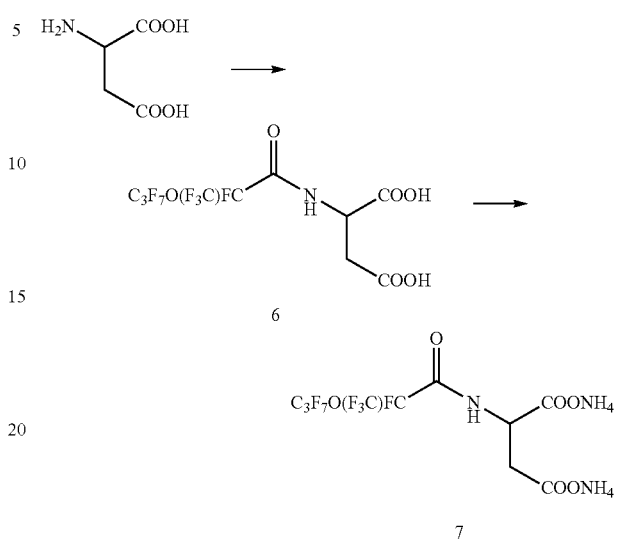

In a manner similar to that of Synthesis Example 2, but using the conditions described in the above scheme, compound 6 (5.6 g, 26%) was synthesized using monoaminosuccinic acid (6.5 g) as a starting material; subsequently, compound 7 (5.7 g, 95%) was obtained.

Synthesis Example 4

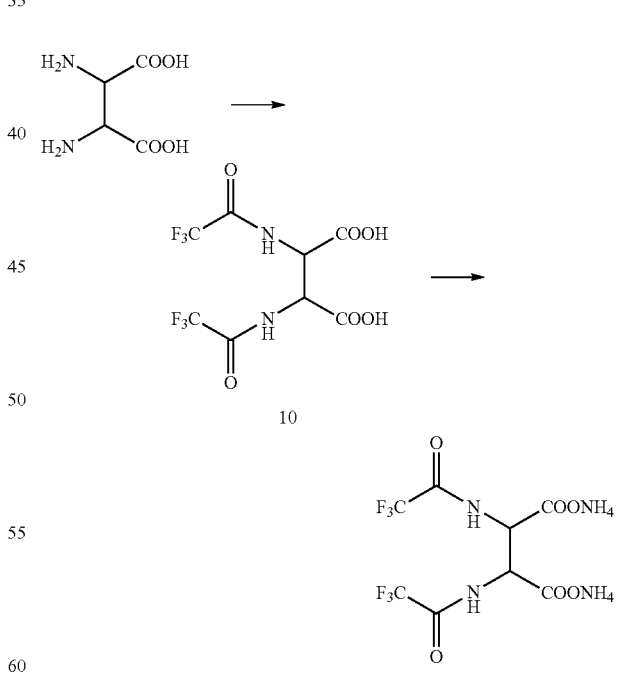

Trifluoroacetic anhydride (17 eq.) was added to a THF solution (5.0 mL) of diamine succinate (0.17 g), and the mixture was stirred for 24 hours. The reaction product solution was concentrated, dissolved in water, and extracted with ethyl acetate. The solvent was distilled off, and the obtained crude product was recrystallized to give compound 10 (0.13 g, 29%).

A 3M ammonia methanol solution (4.0 eq.) was added to a methanol solution (2.0 mL) of compound 10 (0.13 g), and the mixture was stirred at room temperature for 1 hour. Thereafter, the solvent was distilled off to give compound 11 (0.08 g, quamt.).

Synthesis Example 4a

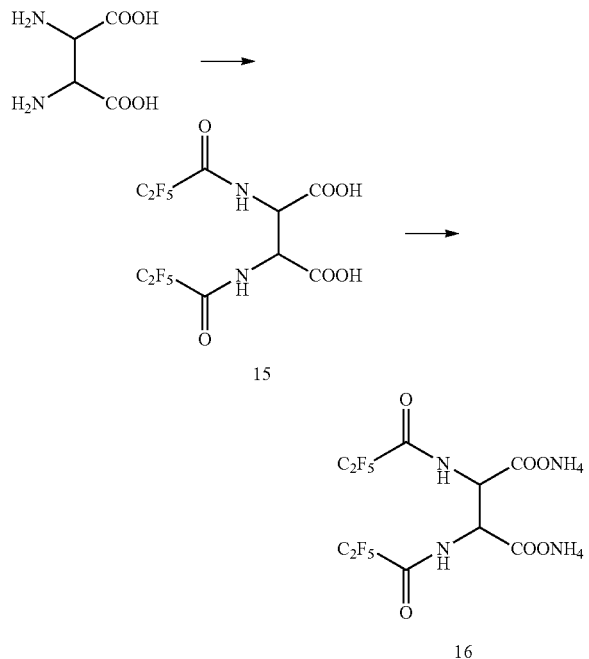

Perfluoropropionic anhydride (13.5 eq.) was added to a THF solution (7.5 mL) of diamine succinate (0.37 g), and the mixture was stirred for 24 hours. The reaction product solution was concentrated, dissolved in water, and extracted with ethyl acetate. The solvent was distilled off, and the obtained crude product was recrystallized to give compound 15 (0.21 g, 20%).

A 3M ammonia methanol solution (4.0 eq.) was added to a methanol solution (2.0 mL) of compound 15 (0.05 g), and the mixture was stirred at room temperature for 1 hour. Thereafter, the solvent was distilled off to give compound 16 (0.004 g, 73%).

Synthesis Example 5

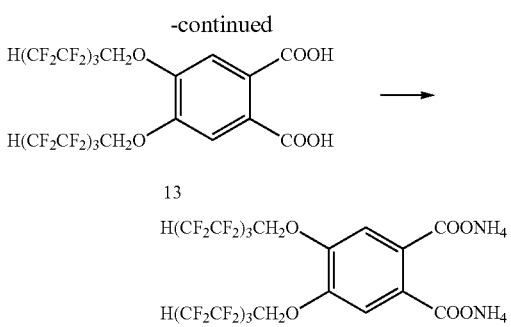

Potassium carbonate (3.0 eq.) and H(CF2CF2)3CH2OH (3.0 eq.) were added to a DMSO solution (5.0 mL) of 4,5-dichlorophthalonitrile (2.1 g), and the mixture was stirred at room temperature for 11 days. Water was added to the reaction product solution, followed by extraction with dichloromethane. The solvent was distilled off. Thereafter, recrystallization was performed to give compound 12 (0.7 g, 9.0%).

Sulfuric acid (9.0 mL) and water (3.0 ml) were added to compound 12, and the mixture was stirred at 150° C. for 3 hours. After the reaction, 150 mL of water was added to the reaction product solution, followed by filtration. The crude product was recrystallized to give compound 13 (0.42 g, 36%).

An ammonia methanol solution (4.0 eq.) was added to a methanol solution (10 mL) of compound 13, and the mixture was stirred at room temperature for 1 hour. Thereafter, the solvent was distilled off to give compound 14 (0.21 g, 61%).

Measurement of Surface Tension

Measurement was performed using an ultrapure water solvent by the Wilhelmy method (plate method), which is a classical method.

The table below shows the results.

TABLE 1

| | NH4 salt surface tension (mN/m) | | |
|---|---|---|---|
| Compound | 1 wt % | 0.1 wt % | 0.01 wt % |
| Compound 7 | 38.4 | 44.8 | 50.7 |
| Compound 9 | 48.9 | 49.7 | 50.2 |
| Compound 11 | 36.2 | 44.8 | 49 |
| Compound 16 | 30.2 | 37.8 | 40 |

The invention claimed is:

1. A branched fluorine-containing compound represented by formula (1):

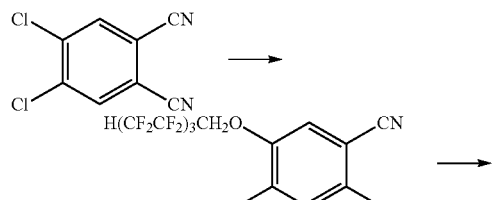

(1)

wherein
L represents
(1) a trivalent carbon-containing linker moiety represented by formula (L-1-1):

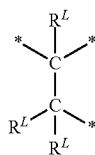

(L-1-1)

wherein $R^L$, in each occurrence, is the same or different and represents hydrogen, alkyl optionally having at least one substituent, $-NH_2$, $-NHR^{RL}$, or $-OR^{RL}$, and $R^{RL}$ represents an organic group, Rf, in each occurrence, is the same or different and represents $C_{1-8}$ fluoroalkyl having at least one ether bond and optionally having at least one substituent selected from the group consisting of nitro, hydroxy, halogen, cyano, aliphatic group, aryl, heterocyclyl, acyl, acyloxy, acylamino, aliphatic oxy, aryloxy, heterocyclyloxy, aliphatic oxycarbonyl, aryloxycarbonyl, heterocyclyloxycarbonyl, carbamoyl, aliphatic sulfonyl, aryl sulfonyl, heterocyclylsulfonyl, aliphatic sulfonyloxy, arylsulfonyloxy, heterocyclylsulfonyloxy, sulfamoyl, aliphatic sulfonamide, arylsulfonamide, heterocyclylsulfonamide, amino, aliphatic amino, arylamino, heterocyclylamino, aliphatic oxycarbonylamino, aryloxycarbonylamino, heterocyclyloxycarbonylamino, aliphatic sulfinyl, arylsulfinyl, arylthio, sulfo, carboxy, aliphatic oxyamino, aryloxyamino, carbamoylamino, sulfamoylamino, sulfamoylcarbamoyl, and carbamoylsulfamoyl, when L is a moiety of formula (L-1-1);

Y, in each occurrence, is the same or different and represents (1) a divalent linking group selected from the group consisting of $-O-$, $-COO-$, $-OCO-$, $-CONR^Y-$, and $-NR^YCO-$ or (2) a bond, with the proviso that when L is a trivalent carbon-containing linker moiety represented by formula (L-1-1), Y is a bond or a divalent linking group selected from $-CONR^Y-$ and $-NR^YCO-$;

$R^Y$, in each occurrence, is the same or different and represents hydrogen or an organic group;

L represents an (n1+n2)-valent carbon-containing linker moiety having at least one carbon atom;

n1 represents a number greater than or equal to 1;
n2 represents a number greater than or equal to 1;
n1+n2 is a number from 3 to 6;

X, in each occurrence, is the same or different and represents a bond;

A, in each occurrence, is the same or different and represents $-ArSO_3M$, $-SO_3M$, $-SO_4M$, $-PO_3M$, or $-COOM$;

M, in each occurrence, is the same or different and represents hydrogen, $-NR_4$, or a metal salt, with the proviso that when A represents $-COOM$, M represents $-NR_4$, or a metal salt; and R represents hydrogen or a $C_{1-4}$ organic group.

2. The branched fluorine-containing compound according to claim 1, wherein L is a trivalent carbon-containing linker moiety represented by formula (L-1-1);

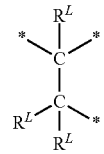

(L-1-1)

wherein $R^L$, in each occurrence, is the same or different and represents hydrogen, alkyl optionally having at least one substituent, $-NH_2$, $-NHR^{RL}$, or $-OR^{RL}$, and $R^{RL}$ represents an organic group, Rf, in each occurrence, is the same or different and represents $C_{1-8}$ fluoroalkyl; and Y, in each occurrence, is $-O-$;

L represents an (n1+n2)-valent carbon-containing linker moiety having at least one carbon atom;

n1 represents a number greater than or equal to 1;
n2 represents a number greater than or equal to 1;
n1+n2 is a number from 3 to 6;

X, in each occurrence, is the same or different and represents a bond;

A, in each occurrence, is the same or different and represents $-ArSO_3M$, $-SO_3M$, $-SO_4M$, $-PO_3M$, or $-COOM$;

M, in each occurrence, is the same or different and represents hydrogen, $-NR_4$, or a metal salt, with the proviso that when A represents $-COOM$, M represents $-NR_4$, or a metal salt; and R represents hydrogen or a $C_{1-4}$ organic group.

3. The branched fluorine-containing compound according to claim 1, wherein L is a trivalent carbon-containing linker moiety represented by formula (L-1-1); and Y, in each occurrence, is the same or different and represents (1) a divalent linking group selected from the group consisting of $-O-$, $-CONR^Y-$, and $-NR^YCO-$ or (2) a bond.

4. The branched fluorine-containing compound according to claim 1, wherein n1 is 1 or 2; and n2 is 2.

5. The branched fluorine-containing compound according to claim 2, wherein n1 is 1 or 2; and n2 is 2.

6. A surfactant comprising the branched fluorine-containing compound according to claim 1.

7. A surfactant comprising the branched fluorine-containing compound according to claim 2.

8. A surfactant comprising the branched fluorine-containing compound according to claim 3.

9. A surfactant comprising the branched fluorine-containing compound according to claim 4.

10. A surfactant comprising the branched fluorine-containing compound according to claim 5.

11. An aqueous dispersant comprising the branched fluorine-containing compound according to claim 1.

12. An aqueous dispersant comprising the branched fluorine-containing compound according to claim 2.

13. An aqueous dispersant comprising the branched fluorine-containing compound according to claim 3.

14. An aqueous dispersant comprising the branched fluorine-containing compound according to claim 4.

15. An aqueous dispersant comprising the branched fluorine-containing compound according to claim 5.

* * * * *